United States Patent [19]

Baggiolini et al.

[11] 4,189,586

[45] Feb. 19, 1980

[54] PREPARATION OF BIOTIN

[75] Inventors: Enrico G. Baggiolini, Nutley; Hsi L. Lee, West Paterson; Milan R. Uskokovic, Upper Montclair, all of N.J.

[73] Assignee: Hoffmann-La Roche Inc., Nutley, N.J.

[21] Appl. No.: 946,675

[22] Filed: Sep. 28, 1978

Related U.S. Application Data

[62] Division of Ser. No. 822,119, Aug. 5, 1977, Pat. No. 4,130,713.

[51] Int. Cl.$^2$ .......................................... C07D 495/04
[52] U.S. Cl. ................................................... 548/303
[58] Field of Search ........................................ 548/303

[56] References Cited

U.S. PATENT DOCUMENTS

| | | | |
|---|---|---|---|
| 2,466,232 | 4/1949 | Harris et al. | 548/303 |
| 2,489,237 | 11/1949 | Goldberg et al. | 548/303 |
| 3,740,416 | 6/1973 | Gerecke et al. | 548/303 |

*Primary Examiner*—Alan L. Rotman
*Assistant Examiner*—Robert C. Whittenbaugh
*Attorney, Agent, or Firm*—Jon S. Saxe; Bernard S. Leon; George W. Johnston

[57] ABSTRACT

A novel procedure for the preparation of biotin employing cysteine as the starting material is disclosed. This synthesis involves the formation of the thiophane ring by a 1,3-dipolar addition. By virtue of this process pure d-biotin can be obtained, thus obviating the need for chemical resolution. Novel intermediates are also disclosed.

3 Claims, No Drawings

PREPARATION OF BIOTIN

This is a division of application Ser. No. 822,119, filed Aug. 5, 1977, now U.S. Pat. No. 4,130,713.

BACKGROUND OF THE INVENTION

This invention relates to a process of preparing biotin from L-(+)-cysteine. Biotin, vitamin H, is a natural product found largely in the kidney, liver, egg yolk, milk and yeast. The compound is used to prevent symptoms of egg-white injury in experimental animals. Its prime medical use is in various dematitides.

Biotin has been prepared synthetically by Harris et al. (Science, 97, 447 (1943) and Baker et al. (J. Org. Chem., 12, 167 (1947), among others. None of these syntheses, however, were commercially feasible. The first commercial synthesis of biotin resulted from the work of Goldberg and Sternbach (U.S. Pat. Nos. 2,489,235 and 2,489,236).

Previous biotin syntheses suffer from the disadvantages that racemic mixtures of intermediates, as well as racemic mixtures of biotin, are formed thus requiring costly and time consuming resolutions. These resolutions also lead to decreased yields of biotin. This disavantage is obviated in the instant invention by use of cysteine as the starting material. Cysteine, a natural amino acid is an optically active compound with the same absolute configuration as the $C_4$-carbon of d-biotin, the biologically active form of biotin. The process of the instant invention proceeds without racemization in forming d-biotin, thus obviating the need for resolution of the final product.

According to the instant invention, biotin is obtained in either the optically pure d-form or as a racemic mixture from a relatively inexpensive starting material. When d-biotin is obtained the need for chemical resolution is obviated. However, in instances where the racemic product is prepared the d-biotin is obtained by conventional resolution procedures.

SUMMARY OF THE INVENTION

This invention is directed to a process for synthesizing d-biotin, which has the structural formula:

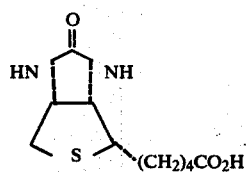

from cysteine, a compound of the formula:

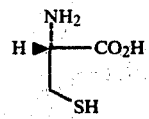

DETAILED DESCRIPTION OF THE INVENTION

The term "alkyl" as used herein, denotes straight or branched chain hydrocarbon groups of 1 to 20 carbon atoms which are saturated or which include one or more double and/or triple carbon to carbon bonds, such as methyl, ethyl, allyl, propargyl, hexenyl and decyl. The term "cycloaliphatic" denotes monocyclic groups of 3 to 7 carbon atoms and polycyclic groups of 5 to 17 carbon atoms, which are saturated or which contain double and/or triple carbon to carbon bonds, such as menthyl, bornyl and cholesteryl.

As further used throughout this application, the term "lower alkyl" denotes straight chain and branched chain saturated aliphatic groups having from 1 to 8 carbon atoms, such as methyl, ethyl, propyl, isopropyl, butyl, isobutyl and the like. As also used herein, the term "aryl" signifies mononuclear aromatic groups, such as phenyl, which can be unsubstituted or substituted in one or more positions with a lower alkylenedioxy, a halogen, a nitro, a lower alkyl or a lower alkoxy substituent and polynuclear aryl groups of 10 to 17 carbon atoms, such as naphthyl, anthryl, phenanthryl and azulyl, which can be substituted with one or more of the aforementioned groups. The preferred aryl groups are the substituted and unsubstituted mononuclear aryl groups, particularly phenyl. As further used herein, the term "aryl lower alkyl" comprehends groups wherein aryl and lower alkyl are as defined above, particularly benzyl. As still further herein, the term "lower alkoxy" comprehends alkoxy groups having from 1 to 7 carbon atoms such as methoxy, ethoxy and the like. Also herein, the term "halogen" or "halo", unless otherwise stated, comprehends fluorine, chlorine, bromine and iodine. Further herein, the term "lower alkylenedioxy" comprehends lower alkylenedioxy groups having 1 to 4 carbon atoms, such as methylenedioxy and ethylenedioxy. The term "alkali" or "alkaline earth metals" denotes sodium, potassium or lithium and calcium, barium or magnesium, respectively. The term "lower alkanols" refers to alkanols having alkyl groups (as defined above) of from 1-8 carbon atoms. The term "lower alkanoic" acid refers to monocarboxylic acids having from 1-8 carbon atoms. The term "lower alkyne" denotes a triply bonded alkyl group containing 1-8 carbon atoms.

As still further used throughout this application, in the pictorial representations of the compounds of this application, a thickened tapered line (◀) indicates a substituent which is in the β-orientation (above the plane of the molecule), a dotted line (---) indicates a substituent which is in the α-orientation (below the plane of the molecule) and a wavy line (∼) indicates a substituent which is in either the α- or β-orientation.

In accordance, with the instant invention, d-biotin is prepared from cysteine in conformity with the following scheme:

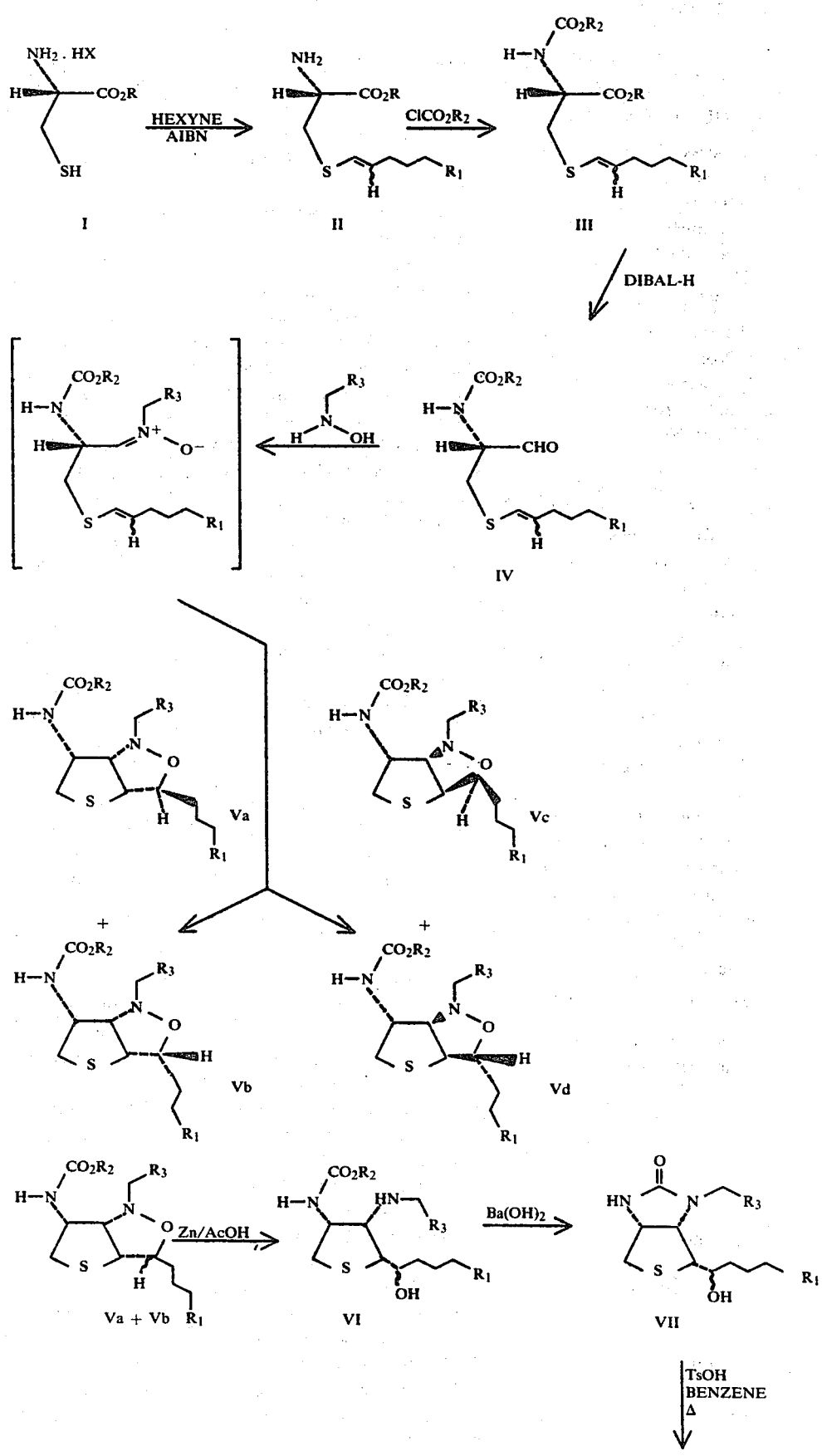

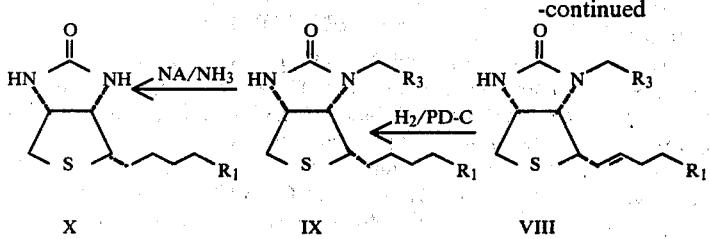

wherein R is hydrogen or lower alkyl, $R_1$ is methyl or —$CH_2OR_4$ where $R_4$ is lower alkyl or benzyl, $R_2$ is lower alkyl, $R_3$ is lower alkyl or substituted and unsubstituted aryl and X is halogen.

Although the above reaction scheme is rather specific, the novel process is in no way to be construed as limiting thereto.

Cysteine is converted to a sulfide of formula II in the above scheme by treatment of the former with an alkyne having at least six carbon atoms. 1-Hexyne is particularly preferred.

The conversion of cysteine to the sulfide of formula II is accomplished by treating the compound of formula I with a lower alkyne, preferably 1-hexyne, in an inert solvent in the presence of a free radical initiator. The reaction is carried out at atmospheric pressure and at a temperature sufficient to cause the formation of free radicals, generally from about 50° C. to about 100° C., preferably 60°–75° C. Typical solvents that may be employed are dioxane, tetrahydrofuran (THF), dimethylformamide (DMF), tetramethylurea, hexamethylphosphoric acid triamide (HMPA). Typical free radical initiators that may be employed are azobisisobutyronitrile (AIBN), peroxides such as di-t-butyl peroxide, benzoyl peroxide, cumyl hydroperoxide and the like.

The sulfide of formula II is then converted to the urethane of formula III in the above scheme by treatment of compound II with an aryl or a lower alkyl haloformate such as methyl chloroformate, ethyl, isopropyl, phenyl or benzyl chloroformates, methyl chloroformate is particularly preferred. This conversion takes place in an inert solvent under conditions of atmospheric pressure and a temperature varying from 0° C. to about 40° C., preferably at about room temperature. The inert solvents that may be employed are those mentioned hereinabove. Tetrahydrofuran is particularly preferred. The conversion is generally carried out under basic conditions. Typical bases that may be employed are alkali metal hydroxides, carbonates and bicarbonates. Sodium carbonate and potassium bicarbonate are particularly preferred. Organic amine bases such as lower alkyl amines, i.e., triethylamine, heterocyclic amines, such as pyridine, s-collidine and the like may also be used.

The compound of formula III is reduced to an aldehyde of formula IV. The reduction is conducted in the presence of an inert solvent employing reducing agents that will selectively reduce the ester group to its corresponding aldehyde. Particularly preferred reducing agents are dialkylaluminum hydrides, particularly diisobutylaluminum hydride (DiBAL) and Li(-3--t-butoxy)AlH$_4$. The reduction is carried out at atmospheric pressure and at temperatures varying from −65° C. to −85° C., preferably −70° C. to −80° C. The inert solvents that may be employed are hexane, heptane, octane, toluene and the like.

The aldehyde of formula IV is then transformed to the isoxazolidines of formula V by treatment of the aldehyde of formula IV with either a lower alkyl or substituted and unsubstituted arylalkyl hydroxylamine. Although any substituted arylalkylhydroxylamine may be employed, benzylhydroxylamine is particularly preferred. The conversion of the aldehyde to the isoxazolidines of formula V proceeds by a 1,3-dipolar addition which results in the formation of a 5,5-bicyclic ring system. This conversion affords predominately intermediates having the proper steric configuration which, upon further conversion(s), as detailed below, will result in all cis d-biotin. The transformation of compound IV to compound V results in four isomers (Va to Vd). The ratio of isomers Va+Vb to Vc+Vd is 62:38. This is a particularly attractive feature of this synthesis because isomers Va and Vb possess the desired all cis thiophane configuration for ultimate obtention of the biologically active biotin. The conversion of the aldehyde to the isoxazolidines takes place in an inert solvent at atmospheric pressure and the reflux temperatures of the solvent. Typical solvents that may be employed are benzene, toluene, xylene, heptane, hexane and the like.

The isoxazolidines of formula Va and Vb are then converted to the tetrahydrothiophenes of formula II by treating said isoxazolidines with either DiBAL or Zn/lower alkanoic acid to effect the ring opening. The conversion, when using Zn/lower alkanoic acid, takes place at atmospheric pressure and at temperatures ranging from 70° C.–100° C., preferably 75° C.–80° C., using the excess lower alkanoic acid from the Zn/lower alkanoic acid catalyst system or a mixture of lower alkanoic acid and water. The preferred lower alkanoic acid is acetic acid. When DiBAL is used to effect the conversion, atmospheric pressure and temperatures of about −65° C. to about −85° C., preferably −75° C., are employed.

The tetrahydrothiophenes of formula VI are then cyclized to the imidazolones of formula VII. The cyclization is conducted in the presence of an alkali or alkaline earth methyl hydroxide at atmospheric pressure and the reflux temperature of the solvent. The preferred base is barium hydroxide, usually used as the monohydrate. The cyclization may be carried out in an inert solvent such as dioxane, tetrahydrofuran or mixtures of either of said ethers with water and the like.

The imidazolones of formula VII are then dehydrated to the imidazolones of formula VIII. The dehydration is conducted in an inert solvent such as benzene, toluene, hexane, heptane, xylene and the like at atmospheric pressure and at temperatures that may be determined by those skilled in the art. Typically employed as dehydration agents are p-toluene sulfonic acid, sulfuric acid, P$_2$O$_5$, SOCl$_2$, H$_3$PO$_4$, activated alumina. Particularly preferred is p-toluenesulfonic acid at the reflux temperature of the solvent.

The imidazolone of formula VIII is then reduced to an imidazolone of formula IX. The reduction of the compound of formula VIII to formula IX is accomplished using Raney nickel, Raney cobalt, supported palladium or platinum—with the support preferably being carbon. This reduction is carried out in a lower alkanol, preferably methanol under hydrogen pressure varying from about 100 psig to about 500 psig preferably 200 psig and at room temperature.

The imidazolone of formula IX is then treated with Na/NH$_3$, or boiling HBr to form the imidazolone of formula X. The conversion of compound IX to compound X is carried out at atmospheric pressure and at a temperature varying from −50° C. to about −90° C., preferably −70° C. The conversion is generally carried out in an inert solvent such as dioxane, THF, and the like.

Compound X may be obtained directly from compound VIII by treating the latter compound with either Raney nickel or palladium on carbon. The direct transformation of compound VIII to compound X may be accomplished under similar conditions employed for the transformation of compound VIII to compound IX.

The conversion of compound X to biotin may be effected in one of two ways depending on the nature of the substituent R. When R is methyl compound X is converted to biotin by microbiological oxidation techniques. The preferred microbiological oxidation is that disclosed in Ogino et al., U.S. Pat. No. 3,859,167, the disclosure of which is incorporated herein by reference. In the Ogino et al. procedure, compound X where R is methyl is converted to biotin by treatment with the organism *Corynebacterium Primorioxydans*.

When R is —CH$_2$OR, with R$_1$ being as previously defined, compound X is converted to biotin by converting the ether to an alcohol by conventional procedures for removing the ether protecting groups. The alcohol that is then formed is converted to the corresponding aldehyde by treatment of said alcohol with Cr$_2$O$_3$/pyridine followed by oxidation to the corresponding lower alkanoic acid with Ag$_2$O.

The preparation of biotin from cysteine as described hereinbefore represents an improvement over the biotin synthesis from cysteine disclosed in Confalone et al., U.S. Pat. No. 3,957,794. The instant procedure is shorter, has significantly higher step yields through the entire procedure than does the aforementioned Confalone process.

The following non-limiting examples are illustrative of the instant invention. All temperatures are in degrees Centigrade.

EXAMPLE 1

A mixture of 12.80 g (68.93 mmol) of DL-cysteine ethyl ester hydrochloride, 25.60 g (311.62 mmol) of 1-hexyne, and 50 mg of 2,2'-azobis-(2-methylpropionitrile) in 250 ml of absolute dioxane was stirred at 60°–65°. under inert gas atmosphere for 20 minutes. After cooling, most of the solvent was evaporated in vacuo. The residue was treated with 150 ml of 1 N sodium carbonate solution and extracted three times with ethyl acetate. The organic phases were combined, washed with 3×50 ml of saturated brine, dried over anhydrous sodium sulfate and evaporated in vacuo to give 15.90 g (99%) of crude (ethyl 2-aminopropanoate-3-yl) (1-hexenyl) sulfide as a thick pale yellow oil which can be used without further purification in the next step. NMR spectroscopical studies showed that the product is approximately a 1:1 mixture of geometrical isomers.

EXAMPLE 2

To a solution of 15.90 g (68.72 mmol) of (ethyl 2-aminopropanoate-3-yl) (1-hexenyl) sulfide obtained from Example 1 dissolved in 100 ml of tetrahydrofuran, 200 ml of a 2 N potassium bicarbonate solution and 200 ml of a 2 N sodium carbonate solution was added. The mixture was cooled at 0° C. and 19.50 g (206.34 mmol) of methyl chloroformate was added dropwise under stirring over the period of 30 minutes. After addition, the reaction mixture was allowed to come to room temperature and further stirred for 2 hours. It was then extracted three times with ethyl acetate and the combined organic phases were washed three times with saturated brine, dried over anhydrous sodium sulfate and evaporated in vacuo to give 17.80 g (89.5%) of crude (ethyl 2-methoxycarbonylaminopropanoate-3-yl) (1-hexenyl)sulfide. This was purified on a 385 g. silica column, using ethyl acetate/hexane as eluent, to give 10.40 g (52.3%) of pure product.

EXAMPLE 3

To a solution of 4.06 g (14.02 mmol) of the (ethyl 2-methoxycarbonylaminopropanoate-3-yl) (1-hexenyl)-sulfide obtained from Example 2 dissolved in 60 ml of absolute toluene cooled at −70° to −78° C., 20.6 ml. (30.0 mmol) of a solution of diisobutylaluminum hydride in toluene (containing 1.5 mmol/ml) precooled at −70° to −78° C. was added dropwise under inert gas atmosphere and over a 30 minute period. At the end of the addition, the reaction mixture was further stirred at −70° to −78° C. for 30 minutes. After this time, 50 ml of a saturated ammonium chloride solution was slowly added dropwise to the reaction mixture which was then allowed to come to room temperature and then extracted three times with ethyl acetate. The combined organic phases were washed three times with saturated brine, dried over anhydrous sodium sulfate, filtered through "celite" and evaporated in vacuo. The residue was dissolved in 50 ml of dichloromethane, filtered through "celite" and evaporated in vacuo to give 3.33 g (97%) of crude (2-methoxycarbonylaminopropanol-3-yl) (1-hexenyl) sulfide which can be used as such in the next step.

EXAMPLE 4

A solution of 3.34 g (13.61 mmol) of (2-methoxycarbonylaminopropanol-3-yl) (1-hexenyl)sulfide obtained from Example 3 and 1.68 g (13.64 mmol) of benzylhydroxylamine in 70 ml of absolute benzene was refluxed in a Dean Stark moisture receiver apparatus. The solvent was then evaporated in vacuo and the mixture of isomeric isoxazolidines obtained was first purified on a 100 g silica column using a mixture of hexane and ethyl acetate (1:1) as eluent to give 3.56 g (74.6%) of a mixture of Va, Vb, Vc, Vd. The component of the mixture were then separated by high pressure liquid chromatography using a Waters Associates chromatograph Model 202 and an 8'×3/8" PORASIS A$_R$ column, eluted with a mixture of hexane and ethyl acetate (5:1) to give the following isomers:

(a) 0.869 g of pure [3R,6S,3S,6R-(3α,3aβ,6β,6aβ)]-3-butyl-3a,5,6,6a-tetrahydro-1-(phenylmethyl)-6-[(methoxycarbonyl)amino]-1H, 3H-thieno[3,2-c]isoxazole(Va). Crystallization from hexane afforded white crystals: m.p. 106°–107° C.

Anal. Calcd for C$_{18}$H$_{26}$N$_2$O$_3$S: C, 61.69; H, 7.48; N, 7.99. Found: C, 61.88; H, 7.51; N, 7.99, (b) 1.202 g of pure [3S,6S,3R,6R-(3β,3aβ,6β,6aβ)]-3-butyl-3a,5,6,6a-tetrahydro-1-(phenylmethyl)-6-[(methoxycarbonyl)amino]-1H,3H-thieno[3,2-c]isoxazole(Vb). Recrystallized from hexane, gave white crystals; m.p. 106°–107° C.

Anal calcd for $C_{18}H_{26}N_2O_3S$: C, 61.69; H, 7.48; N, 7.99. Found: C, 61.90; H, 7.70; N, 7.69, (c) 0.419 g of pure [(3S,6S, 3R,6R-(3β,3aα,6β,6aα)]-3-butyl-3a,5,6,6a-tetrahydro-1-(phenylmethyl)-6-[(methoxycarbonyl)amino]-1H,3H-thieno[3,2-c]isoxazole(Vd). Crystallized from hexane, gave white crystals: m.p. 67°–68° C.

Anal calcd for $C_{18}H_{26}N_2O_3S$: C, 61.99; H, 7.48; N, 7.99. Found: C, 61.70; H, 7.53; N, 7.94, and (d) 0.805 g of pure [3R,6S,3S,6R-(3α,3aα,6β,6aα)]-3-butyl-3a,5,6,6a-tetrahydro-1-phenylmethyl)-6-[(methoxycarboyl)amino]-1H,3H-thieno [3,2-c]isoxazole(Vc). Crystallized from hexane, gave white crystals: m.p. 107°–107.5°. Anal. Calcd for $C_{18}H_{26}N_2O_3S$: C, 61.69; H, 7.48; N, 7.99. Found: C, 61.76; H, 7.63; N, 7.69.

EXAMPLE 5

A suspension of 0.576 g (1.64 mmol) of the isoxazole (a) of Example 4, 1.5 g of zinc dust in 20 ml of 50% acetic acid was stirred at 75°–80° C. for 20 hours. The reaction mixture was then filtered and the solvent evaporated in vacuo. The residue was treated with 50 ml of a 2 N sodium carbonate solution which was then extracted three times with ethyl acetate. The combined organic phases were washed three times with saturated brine, dried over anhydrous sodium sulfate, filtered, and evaporated to dryness to give 0.566 g (98% yield) of crude [2R-(2R* ),3R,4S,2S-(2S*),3S,4R]-α-butyltetrahydro-4-[(methoxycarbonyl)amino]-3-[(phenylmethyl)amino]-2-thiophenemethanol. Crystallization from ether afforded 0.508 g (89% yield) of pure product, m.p. 88°–89° C.

Anal. Calcd for $C_{18}H_{28}N_2O_3S$: C, 61.33; H, 8.01; N, 7.95. Found: C, 61.41; H, 8.21; N, 7.61.

EXAMPLE 6

A suspension of 0.905 g (2.58 mmol) of the product (b) of Example 4, 2.0 g of zinc dust in 40 ml of 50% acetic acid was stirred at 75°–80 ° C. for 20 hours. The reaction mixture was then filtered and the solvent evaporated in vacuo. The residue was treated with 50 ml of a 2 N sodium carbonate solution which was then extracted three times with ethyl acetate. The combined organic phases were washed three times with saturated brine, dried over anhydrous sodium sulfate, filtered, and evaporated to dryness to give 0.902 g (99% yield) of crude [2R-(2S*),3R,4S,2S-(2R*)3S,4R]-α-butyltetrahydro-4-[(methoxycarbonyl)amino]-3-[(phenylmethyl)amino]-2-thiophenemethanol. Crystallization from ether gave 0.849 g (93% yield) of pure product, m.p. 121°–122° C.

Anal. Calcd. for $C_{18}H_{28}N_2O_3S$: C, 61.33; H, 8.01; N, 7.95. Found: C, 61.42; H, 8.14; N, 7.82.

EXAMPLE 7

A mixture of 0.820 g (2.32 mmol) of the product of Example 5, 2.0 g of barium hydroxide monohydrate, 30 ml of water, and 20 ml of dioxane was refluxed for 2 hours. After cooling, the reaction mixture was saturated with sodium chloride and extracted four times with ethyl acetate. The combined organic phases were washed three times with saturated brine, dried over anhydrous sodium sulfate, and evaporated in vacuo to give 0.650 g (87%) of crude [4R,4S-(3aβ,4β(R*), (S*), 6aβ)]-3a,4,6,6a-tetrahydro-4-(1-hydroxypentyl)-3-(phenylmethyl)-1H-thieno[3,4-d]imidazol-2(3H)-one. Crystallization from ethermethylene chloride gave 0.569 g (66%) of pure product, m.p. 174°–175° C.

Anal. Calcd for $C_{17}H_{24}N_2O_2S$: C, 63.72; H, 7.55; N, 8.74. Found: C, 63.88; H, 7.73; N, 8.86.

EXAMPLE 8

A mixture of 0.888 g (2.52 mmol) of the product of Example 6, 1.5 g of barium hydroxide monohydrate, 30 ml of water, and 25 ml of dioxane was refluxed for 1½ hours. After cooling, the reaction mixture was acidified with 2 N hydrochloric acid and extracted three times with ethyl acetate. The combined organic phases were washed three times with saturated brine, dried over anhydrous sodium sulfate, and evaporated in vacuo and crystallized from ether-methylene chloride to give 0.741 g (92%) of pure [4R,4S-(3aβ,4β(S*),(R*),6aβ)]-3a,3,6,6a-tetrahydro-4-(1-hydroxypentyl)-3-(phenylmethyl)-1H-thieno[3,4-ol]imidazole-2(3H)-one, m.p. 190°–191° C.

Anal. Calcd for $C_{17}H_{24}N_2O_2S$: C, 63.72; H, 7.55; N, 8.74. Found: C, 63.55; H, 7.60; N, 8.81.

EXAMPLE 9

A solution of 0.400 g (1.25 mmol) of the product Example 7 0.356 mg (1.87 mmol) of p-toluenesulfonic acid in 40 ml of absolute toluene was refluxed for 9 hours. After cooling, the reaction mixture was diluted with 100 ml of ethyl acetate washed with three times each 2 N sodium carbonate solution and saturated brine, dried with anhydrous sodium sulfate, filtered, and evaporated in vacuo to give 0.395 g of crude [4R,4S-(3aβ,4β, 6aβ)]-3a,4,6,6a-tetrahydro-3-(phenylmethyl)-4-(1-pentyl)-1H-thieno[3,4-d]imidazol-2(3H)-one. Two crystallization from ether afforded 0.149 g (40%) of pure product, m.p. 92°–93° C. The mother liquors still contain large amounts of product together with the corresponding cis isomer, which can be used as such in the next step.

Anal. Calcd for $C_{17}H_{22}N_2OS$: C, 67.51; H, 7.33; N, 9.26. Found: C, 67.45; H, 7.12; N, 9.09.

EXAMPLE 10

A solution of 0.727 g (2.27 mmol) of the product of Example 8, 0.615 g (3.23 mmol) of p-toluenesulfonic acid in 60 ml absolute toluene was refluxed for nine hours. After cooling the reaction mixture was diluted with 100 ml. of ethyl acetate, washed three times each with a 2N sodium carbonate solution and saturated brine, dried with anhydrous sodium sulfate, filtered, and evaporated in vacuo to give 0.678 g of crude product. This was crystallized twice from ether to give 0.391 g (57% yield) of pure product. The mother liquor still contains large amounts of product together with its corresponding cis isomer which can be used as such in the next step.

EXAMPLE 11

A suspension of 0.235 g (0.78 mmol) of the product of Examples 9 and 10, 150 mg. of 10% palladium-on-charcoal in 50 ml of methanol was hydrogenated at room temperature and uder 200 lbs. pressure for 20 hours. The reaction mixture was then filtered and evaporated in vacuo to give 0.227 g of crude [4R,4S-(3aβ, 4β,6aβ)]-3a,4,6,6a-tetrahydro-3-(phenylmethyl)-4-pentyl-1H- thieno 3,4-d imidazol-2(3H)-one. Crystallization from ethermethylene chloride gave 0.195 g (82%) of white crystals, m.p. 129°–131° C.

Anal. Calcd for $C_{17}H_{24}N_2OS$: C, 67.07; H, 7.94; N, 9.20. Found: C, 66.76; H, 7.88; N, 9.21.

EXAMPLE 12

To a solution of 0.100 g (0.328 mmol) of the product of Example 11, 10 ml of absolute tetrahydrofuran and 20 ml of liquid ammonia (distilled from sodium) kept at −70° C., small pieces of sodium were continuously added during 1 hour, so that the blue color of the solution persists. After this time, a few crystals of ammonium chloride were added until the blue color disappears. Then again, small pieces of sodium were added, until the blue color of the solution persists for three hours. After that, a few crystals of ammonium chloride were added and the reaction mixture allowed to come to room temperature and the ammonia to evaporate. The residue was treated with 50 ml of saturated ammonia chloride solution and extracted three times with ethyl acetate. The combined organic phases were washed three times with brine, dried over anhydrous sodium sulfate, filtered, and evaporated in vacuo to give 0.070 g of crude [4R,4S-(3a$\beta$,4$\beta$,6a$\beta$)]-3a,4,6,6a-tetrahydro-4-pentyl-1H-thieno[3,4-d]imidazol-2(3H)-one. Crystallization from methylene chloride gave 0.057 g (81%) of white crystals, m.p. 144°–145° C.

Anal. Calcd for $C_{10}H_{18}N_2OS$: C, 56.04; H, 8.46; N, 13.07. Found: C, 55.96; H, 8.33; N, 12.63.

We claim:

1. A compound of the formula:

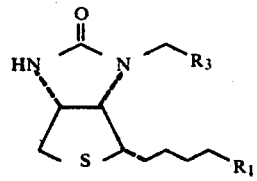

IX or the racemate thereof, wherein $R_1$ is methyl or —CH$_2$OR$_4$, where $R_4$ is lower alkyl or benzyl; and $R_3$ is aryl selected from the group consisting of phenyl, naphthyl, anthryl, phenanthryl and azulyl, said aryl being unsubstituted or substituted in one or more positions with lower alkylenedioxy, halogen, nitro, lower alkyl or lower alkoxy.

2. The compound of claim 1 wherein $R_1$ is methyl and $R_3$ is phenyl.

3. The compound of claim 1 wherein $R_3$ is phenyl.